US012636427B2

(12) United States Patent
Lee et al.

(10) Patent No.: US 12,636,427 B2
(45) Date of Patent: May 26, 2026

(54) CYLINDER PUMP

(71) Applicant: MEINNTECH CO. LTD., Anyang-si (KR)

(72) Inventors: Kun Hyung Lee, Seoul (KR); Sang Bin Lee, Seoul (KR); Ji Eun Lee, Seoul (KR); Jong Hyung Eom, Bucheon-si (KR)

(73) Assignee: MEINNTECH CO., LTD., Anyang-si (KR)

( * ) Notice: Subject to any disclaimer, the term of this patent is extended or adjusted under 35 U.S.C. 154(b) by 927 days.

(21) Appl. No.: 17/910,010

(22) PCT Filed: Nov. 9, 2020

(86) PCT No.: PCT/KR2020/015624
§ 371 (c)(1),
(2) Date: Sep. 8, 2022

(87) PCT Pub. No.: WO2021/182710
PCT Pub. Date: Sep. 16, 2021

(65) Prior Publication Data
US 2023/0129878 A1 Apr. 27, 2023

(30) Foreign Application Priority Data

Mar. 10, 2020 (KR) ........................ 10-2020-0029717

(51) Int. Cl.
*A61M 5/142* (2006.01)
*A61M 5/172* (2006.01)
*A61M 5/38* (2006.01)

(52) U.S. Cl.
CPC ........ *A61M 5/14216* (2013.01); *A61M 5/172* (2013.01); *A61M 5/38* (2013.01)

(58) Field of Classification Search
CPC .... A61M 5/14216; A61M 5/172; A61M 5/38; A61M 5/1422; A61M 5/165;
(Continued)

(56) References Cited

U.S. PATENT DOCUMENTS 4,529,401 A * 7/1985 Leslie ................. A61M 5/1456
604/67
4,702,829 A 10/1987 Polaschegg et al.
(Continued)

FOREIGN PATENT DOCUMENTS

CN 209645558 U 11/2019
JP 2004-24874 A 1/2004
(Continued)

OTHER PUBLICATIONS

Machine Translation of KR 10-0948632 (specification only) (Year: 2010).*
(Continued)

*Primary Examiner* — James D Ponton
(74) *Attorney, Agent, or Firm* — LRK PATENT LAW FIRM

(57) ABSTRACT

The present invention relates to a cylinder pump including: a body part having a main body with a coupling groove formed thereon and a front body coupled to the main body by means of hinges; a cartridge detachably attached to the coupling groove of the body part; a driving part located inside the main body to operate the cartridge; a display part located on the front body to provide an interface necessary for the operation thereof; a controller for controlling the operation of the driving part; and an operating part for transmitting a user's operating signal or input information to the controller.

9 Claims, 13 Drawing Sheets

200

(58) Field of Classification Search
CPC .... A61M 2205/121; A61M 2205/6045; A61M 5/1452; A61M 5/142; A61M 5/16877; A61M 2005/14208; A61M 2005/1657
See application file for complete search history.

(56) References Cited

U.S. PATENT DOCUMENTS

| | | | |
|---|---|---|---|
| 5,308,333 A | 5/1994 | Skakoon | |
| 2004/0057855 A1* | 3/2004 | Gerlach | A61M 5/142 |
| | | | 417/469 |
| 2012/0215200 A1 | 8/2012 | Matsuura et al. | |

FOREIGN PATENT DOCUMENTS

| | | | |
|---|---|---|---|
| KR | 10-2008-0027357 B1 | 3/2008 |
| KR | 10-0827496 B1 | 5/2008 |
| KR | 10-0948632 B1 | 3/2010 |
| KR | 10-1039058 B1 | 6/2011 |
| KR | 10-2014-0132836 A | 11/2014 |
| KR | 10-1955437 B1 | 3/2019 |
| WO | 2015/020374 A1 | 2/2015 |
| WO | 2019-038751 A1 | 2/2019 |

OTHER PUBLICATIONS

JPO Office Action, dated Aug. 15, 2023, for Japanese Patent Application No. 2022-554932 which corresponds to the identified U.S. application.
CHIPA Office Action, dated Oct. 26, 2023, for Chinese Patent Application No. 202080098374.5 which corresponds to the identified U.S. application.
Search Report, mailed Feb. 25, 2021, for International Application No. PCT/KR2020/015624.
Written Opinion, mailed Feb. 25, 2021, for International Application No. PCT/KR2020/015624.
European Search Report, mailed Mar. 6, 2024, for International Application No. PCT/KR2020015624.

* cited by examiner (a)                    (b)

200

300

300

(a)

(b)

(a)                                          (b)

(a)                          (b)

(a)

(b)

(c)

800

CYLINDER PUMP

CROSS-REFERENCE TO RELATED APPLICATIONS

The present application is a U.S. National Phase entry from International Application No. PCT/KR2020/015624, filed on Nov. 9, 2020, which claims priority to Korean Patent Application No. 10-2020-0029717,filed on Mar. 10, 2020, the disclosure of which is incorporated by reference herein in their entirety.

TECHNICAL FIELD

The present invention relates to a cylinder pump, and more specifically, to a cylinder pump that is capable of injecting a chemical liquid or blood into a patient's body stably with a high degree of precision, irrespective of the position of a chemical liquid container or blood pack, while being not used dividedly into an infusion pump and a syringe pump as drug injection pumps.

BACKGROUND ART

In the case where excessive bleeding is caused by a disease, accident, or operation, a disease occurs due to infection or a weakened immune system, or lack of electrolytes or nutrition in the body occurs, blood, a fluid, an amino acid liquid, a glucose solution, or a drug is generally injected into a patient's body so as to compensate for the lacks of blood and electrolytes or nutrition or treat the disease.

In conventional practices, a syringe pump, an infusion pump, or a mechanical type pump is usually used to inject the chemical liquid or blood stored in a chemical liquid container or blood pack into the patient's body, while constantly controlling an injection amount with a high degree of precision.

In this case, the syringe pump is configured to push a plunger of a syringe to thus inject the chemical liquid or blood into the patient's body, and so as to precisely adjust the amount of chemical liquid or blood injected into the patient's body, the infusion pump is configured to allow a chemical liquid container to be hung at a given height to pressurize an infusion set tube through the interlocking operation of a terminal thereof under gravity. In this case, however, only when the syringe pump or the infusion pump is fixedly located at the same position as the chemical liquid container, the chemical liquid or blood may be injected with a given degree of precision.

In specific, the infusion pump is configured to allow the terminal to pressurize the tube so that the chemical liquid or blood is injected into the patient's body, and in this case, PVC tubes pressurized against the terminal may have different elasticity according to manufacturing companies and be greatly influenced by external temperatures, so that they cannot be controlled precisely, thereby making it hard to constantly maintain their performance.

In the case where the syringe pump is used, further, the amount of chemical liquid or blood injected can be precisely controlled, but as the amount of chemical liquid or blood injected is controlled through the syringe, there is a limitation in injecting a large amount of chemical liquid or blood. If it is desired to inject the large amount of chemical liquid or blood, accordingly, the syringe has to be frequently exchanged with new one, and because it is impossible to inject a tiny amount of chemical liquid, further, a lot of drugs have to be mixed before the injection. Besides, infection and contamination may occur in a process of repeatedly operating the syringe pump.

In a process of treating lots of syringes together with medical waste and burning them, dioxins causing cancer are emitted, and accordingly, it is necessary to carefully treat the syringes after their use. Further, the syringe pump requires a relatively long operating time until the chemical liquid is injected, thereby undesirably causing medical accidents such as blocking, and the like or side effects.

Above all, the conventional infusion or syringe pump operates in the mechanical interlocking way or the indirect control way using the plunger when injects the chemical liquid or blood into the patient's body, so that undesirably, there is a high possibility that careless or incidental medical accidents or malfunctions may occur, and labors (nurses, etc.) for managing the infusion or syringe pump have to be periodically needed. Therefore, there is a definite need to develop a new drug injection device that operates in a direct control way to solve the problems occurring when the conventional infusion or syringe pump is used.

PRIOR ART LITERATURE

Patent Literature (Patent literature 1) Korean Patent No. 10-0948632

DISCLOSURE

Technical Problem

Accordingly, the present invention has been made to solve the above-mentioned problems occurring when the chemical liquid or blood is injected into the patient's body through the infusion or syringe pump, and it is an object of the present invention to provide a cylinder pump that is capable of injecting a chemical liquid or blood into a patient's body constantly in real time with a high degree of precision by means of the utilization of a cylinder cartridge, irrespective of the position and size of a chemical liquid container or blood pack, while not dispensing the chemical liquid stored in the chemical liquid container or syringe or the blood stored in the blood pack.

The technical problems to be achieved through the present invention are not limited as mentioned above, and other technical problems not mentioned herein will be obviously understood by one of ordinary skill in the art through the following description.

Technical Solution

To accomplish the above-mentioned objects, according to the present invention, there is provided a cylinder pump including: a body part having a main body with a coupling groove formed thereon and a front body coupled to the main body by means of hinges; a cartridge detachably attached to the coupling groove of the body part; a driving part located inside the main body to operate the cartridge; a display part located on the front body to provide an interface necessary for the operation thereof; a controller for controlling the operation of the driving part; and an operating part for transmitting a user's operating signal or input information to the controller.

According to the present invention, the cartridge may include: an upper housing having an upper rotation member inserted thereinto; and a lower housing coupled to the upper housing and having a lower rotation member inserted there-into, wherein the upper rotation member has an upper rotation member hole formed thereon, the lower rotation member has a lower rotation member hole formed thereon, and by the inner peripheral surfaces of the upper housing and the lower housing and the outer peripheral surfaces of the upper rotation member and the lower rotation member, a donut-shaped cylinder is formed, the donut-shaped cylinder having an inlet connected thereto to introduce a chemical liquid or blood thereinto, an outlet connected thereto to discharge the chemical liquid or blood therefrom to the outside, and a first piston and a second piston rotating therein.

According to the present invention, the driving part may include: a driving part body; a first driving motor and a second driving motor coupled to the driving part body; a first worm and a second worm operating by means of the first driving motor and the second driving motor, respectively; a first worm gear and a second worm gear operating engagedly with the first worm and the second worm, respectively; an inner driving gear rotating by means of the first worm gear; and an outer driving gear rotating by means of the second worm gear.

According to the present invention, the upper rotation member hole may have the shape of a cross having different widths and the lower rotation member hole may have the shape of T.

According to the present invention, the outer driving gear may have the shape of a cross having different widths and be coupled to the upper rotation member, and the inner driving gear may have the shape of T and be coupled to the lower rotation member.

According to the present invention, the controller may acquire the coordinates of the first piston and the second piston located inside the cartridge to display the acquired coordinates on the display part.

According to the present invention, the controller may control the driving part to allow the first piston and the second piston of the cartridge to be located at the outsides of the inlet and the outlet so that the chemical liquid or blood freely flows from the cartridge.

According to the present invention, the controller may control the driving part to allow the first piston of the cartridge to be located between the inlet and the outlet so that no chemical liquid or blood freely flows from the cartridge.

According to the present invention, at least one of the inlet and the outlet may have a membrane filter mounted thereon to remove air from the chemical liquid.

According to the present invention, the membrane filter may include a hydrophilic membrane filter for passing the chemical liquid therethrough, not passing air therethrough, and a hydrophobic membrane filter for emitting the air not passing through the hydrophilic membrane filter to the outside.

Advantageous Effects

According to the present invention, the cylinder pump is configured to inject the chemical liquid or blood into the patient's body, irrespective of the installation position of the chemical liquid container or blood pack, so that the cylinder pump can be freely set in position.

According to the present invention, further, the cylinder pump is configured to inject the chemical liquid or blood stored in the chemical liquid container (or blood pack) and the syringe into the patient's body, without having any separate device, so that various types of conventional chemical liquid injection devices may be replaced with the cylinder pump according to the present invention.

The effectiveness of the present invention is not limited as mentioned above, and it should be understood to those skilled in the art that the effectiveness of the present invention may include another effectiveness as not mentioned above from the detailed description of the present invention.

MODE FOR INVENTION

Figure 1:
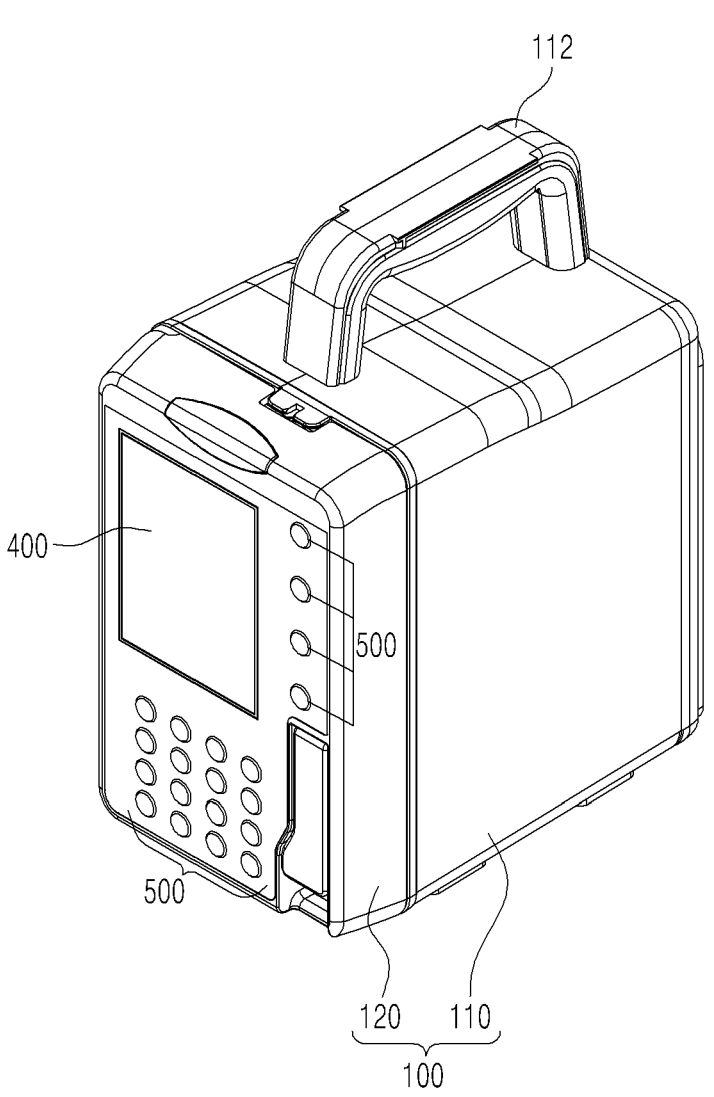
FIG. 1 is a perspective view showing a cylinder pump according to the present invention.

The present invention is disclosed with reference to the attached drawings wherein the corresponding parts in the embodiments according to the present invention are indicated by corresponding reference numerals. If it is determined that the detailed explanation on the well known technology related to the present invention makes the scope according to the present invention not clear, the explanation will be avoided for the brevity of the description.

When it is said that one element is described as being "connected" or "coupled" to the other element, one element may be directly connected or coupled to the other element, but it should be understood that another element may be present between the two elements. In the description, when it is said that one member is located "above" or "under" another member, it means that one member may come into contact with another member as well as yet another member may exist between the two members.

In this application, terms, such as "comprise", "include", or 'have", are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

Hereinafter, an explanation of a cylinder pump according to the present invention will be given in detail with reference to FIGS. 1 to 3b.

Figure 2:
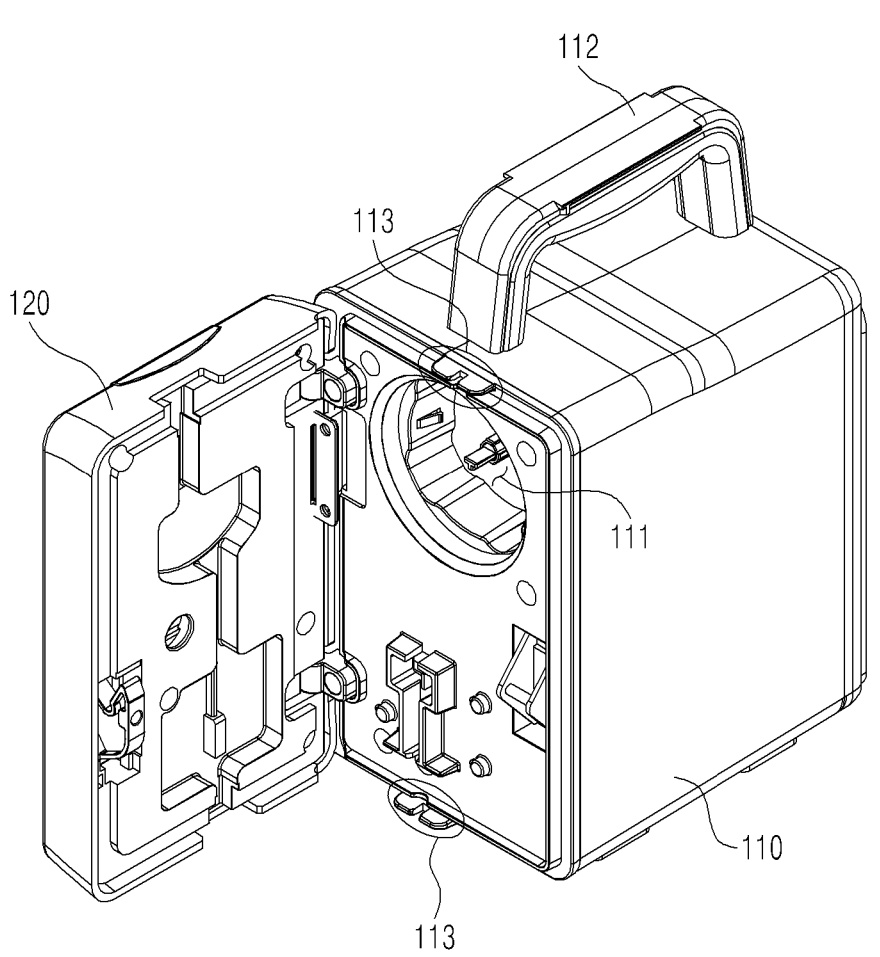
FIG. 2 is a perspective view showing an open body part of the cylinder pump according to the present invention.
Figure 3:
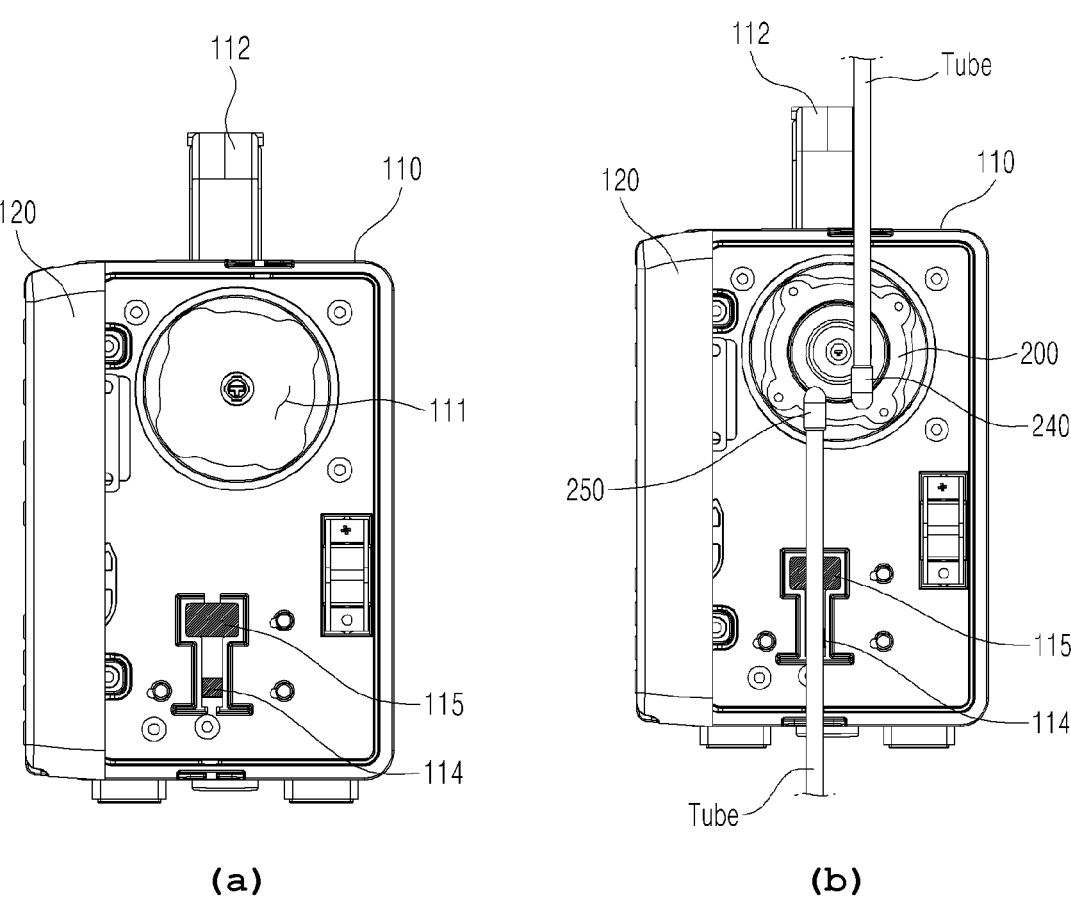
FIGS. 3a and 3b are front views showing a main body and a cartridge coupled to the main body of the cylinder pump according to the present invention.

FIG. 1 is a perspective view showing a cylinder pump according to the present invention, FIG. 2 is a perspective view showing an open body part of the cylinder pump according to the present invention, and FIGS. 3a and 3b are front views showing a main body and a cartridge coupled to the main body of the cylinder pump according to the present invention.

In the conventional practices, the infusion pump or syringe pump is generally used to inject the chemical liquid or blood into the patient's body, but in the case of the infusion pump or syringe pump, there is a high possibility that a machine for pressurizing the tube or a device for horizontally moving a plunger may be malfunctioned. To inject the chemical liquid stored in a chemical liquid container into the patient's body, the infusion pump has to be used, and to inject the chemical liquid stored in a syringe, the syringe pump has to be used. Accordingly, such different injection devices have to be prepared according to the types of containers for storing the chemical liquid or blood (that is, the chemical liquid container and the syringe).

Therefore, the present invention provides a different type of cylinder pump from the conventional pumps, thereby desirably overcoming the problems the conventional infusion or syringe pump has had.

A cylinder pump according to the present invention includes a body part 100 constituted of a main body 110 and a front body 120, a cartridge 200 detachably mounted into the body part 100, a driving part 300 for operating the cartridge 200 to allow a chemical liquid or blood to be introduced into the cartridge 200 or discharged from the cartridge 200 to the outside of the cartridge 200, and a controller (not shown) for controlling the operation of the driving part 300.

Now, explanations of the parts constituting the cylinder pump according to the present invention will be given in detail. First, the body part 100 includes the main body 110 having a coupling groove 111 to which the cartridge 200 is detachably attached and the front body 120 coupled to the main body 110 by means of hinges and serving as a door, as shown in FIG. 2.

The driving part 300 is located inside the main body 110, and some components of the driving part 300 are exposed to the outside from the coupling groove 111 formed on the front surface of the main body 110. Accordingly, as shown in FIGS. 3a and 3b, the cartridge 200 is detachably attached to the coupling groove 111, and through the formation of the coupling groove 111 on the main body 110, the cartridge 200 is protected by means of the front body 120 and the main body 110.

In this case, the main body 110 has a handle 112 grasped by a user such as a doctor, a nurse, and the like, so that he or she can move the cylinder pump according to the present invention conveniently.

Further, a syringe is fixed to the handle 112, and accordingly, the chemical liquid or blood stored in the syringe is injected into a patient's body through the cylinder pump according to the present invention. An explanation of such a process will be described later.

Referring to FIGS. 1 to 3b, the handle 112 is located on top of the main body 110, but without being limited thereto, the handle 112 may be disposed on a left or right side of the main body 110.

Further, the front body 120 has a display part 400 for providing an interface necessary to operate the cylinder pump according to the present invention and an operating part 500 for transmitting the user's control signal or input information to the controller for controlling the operation of the driving part 300. Accordingly, the user sees the interface provided through the display part 400 and operates the operating part 500 to control the operation of the driving part 300.

For example, the operating part 500 includes a purge key for performing a purge function and a bolus key for performing a bolus function. If the purge key is pressed by the user, the driving part 300 is controlled by the controller to remove the air bubbles formed in the tubes connected to the cartridge 200 so that the chemical liquid or blood is introduced into the cartridge 200 as soon as possible, and further, if the bolus key is pressed by the user, the chemical liquid or blood is injected into patient's body at pre-determined injection speed and amount.

The operating part 500 includes the purge key and the bolus key, as mentioned above, but without being limited thereto, the operating part 500 may further include number keys for controlling injection amount, injection time, and injection speed, a pump reset key, a control key, and the like.

Next, the cartridge 200 detachably attached to the body part 100 (particularly the main body 110), through which the chemical liquid or blood stored in a chemical liquid container, a blood pack, or a syringe is introduced, discharged again to the outside, and injected into the patient's body, will be described with reference to FIGS. 3a to 6.

Figure 4:
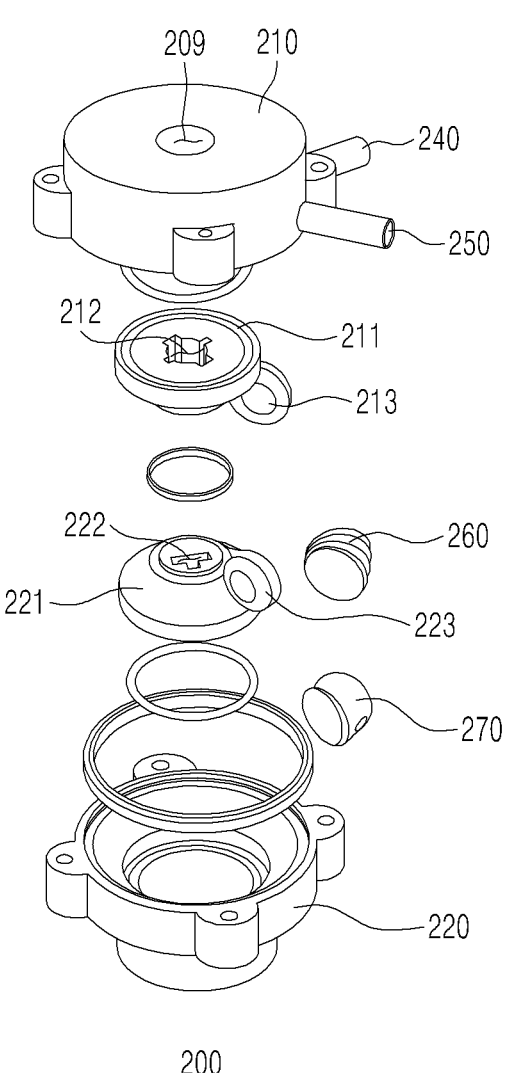
FIG. 4 is an exploded perspective view showing the cartridge coupled to the cylinder pump according to the present invention.
Figure 5:
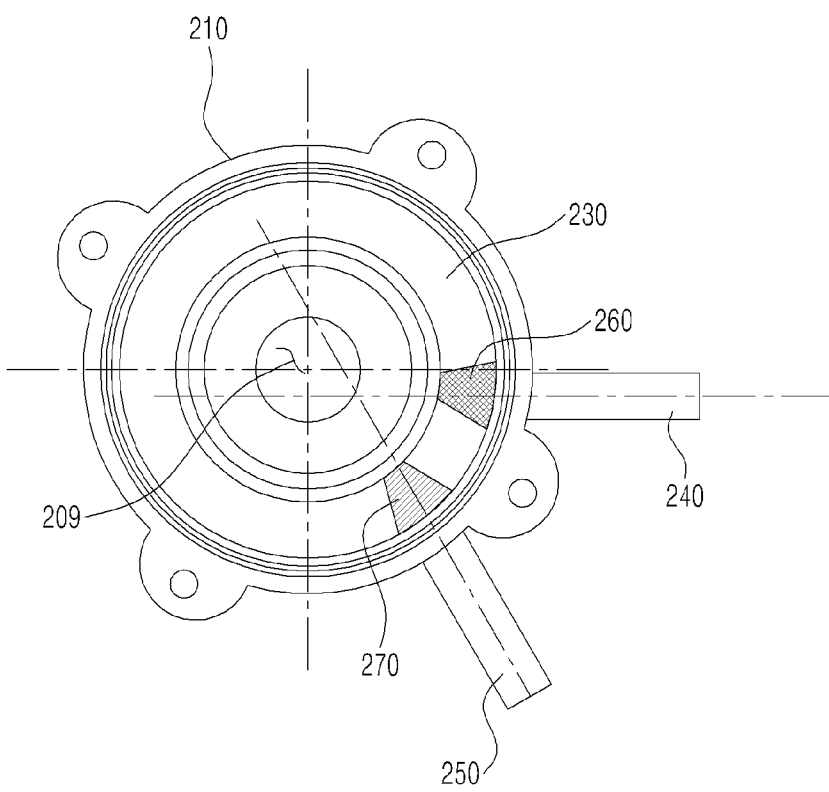
FIG. 5 is a bottom view showing an upper housing of the cartridge of the cylinder pump according to the present invention.
Figure 6:
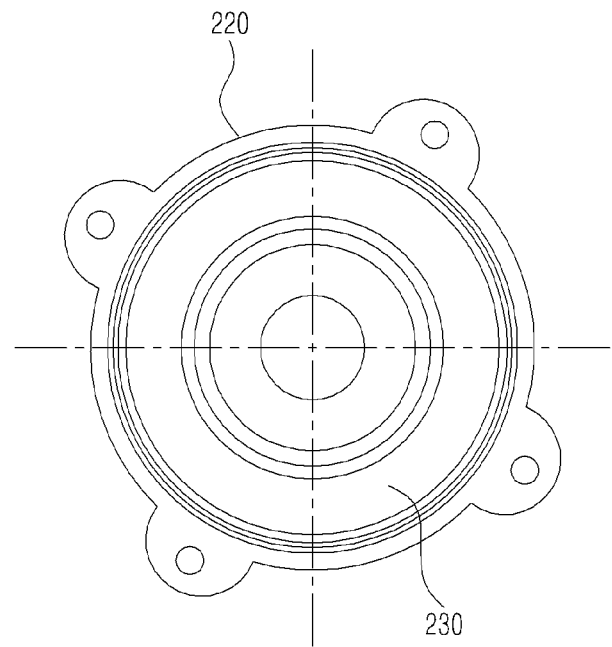
FIG. 6 is a plan view showing a lower housing of the cartridge of the cylinder pump according to the present invention.

FIG. 4 is an exploded perspective view showing the cartridge coupled to the cylinder pump according to the present invention, FIG. 5 is a bottom view showing an upper housing of the cartridge of the cylinder pump according to the present invention, and FIG. 6 is a plan view showing a lower housing of the cartridge of the cylinder pump according to the present invention.

As shown in FIGS. 4 to 6, the cartridge 200 includes an upper housing 210 having an upper rotation member 211 inserted thereinto and a lower housing 220 coupled to the upper housing 210 and having a lower rotation member 221 inserted thereinto. Further, a donut-shaped cylinder 230 is formed by means of the inner peripheral surfaces of the upper housing 210 and the lower housing 220 and the outer peripheral surfaces of the upper rotation member 211 and the lower rotation member 221.

Further, an inlet 240 is connected to the cylinder 230 to introduce the chemical liquid or blood into the cylinder 230, and an outlet 250 is connected to the cylinder 230 to discharge the chemical liquid or blood from the cylinder 230 to the outside. Tubes are connected to the inlet 240 and the outlet 250, respectively, to move the chemical liquid or blood.

Moreover, the cylinder 230 has a first piston 260 and a second piston 270 disposed therein to rotate by means of the driving part 300. As the first piston 260 and the second piston 270 operate, the chemical liquid or blood is introduced into the cylinder 230 through the inlet 240 and discharged from the cylinder 230 to the outside through the outlet 250.

In specific, an upper pushing member 213 is formed integrally with the upper rotation member 211, and a lower pushing member 223 is formed integrally with the lower rotation member 221. As a result, the first piston 260, which comes into contact with the upper pushing member 213 of the upper rotation member 211, rotates by means of the rotation of the upper rotation member 211, and the second piston 270, which comes into contact with the lower pushing member 223 of the lower rotation member 221, rotates by means of the rotation of the lower rotation member 221.

In this case, as shown in FIG. 4, the upper housing 210 has an upper housing hole 209 formed thereon, the upper rotation member 211 has an upper rotation member hole 212 formed thereon, and the lower rotation member 221 has a lower housing hole 222 formed thereon. Accordingly, the cartridge 200 is coupled to the driving part 300, and the first piston 260 and the second piston 270 of the cartridge 200 coupled to the driving part 300 rotate inside the cylinder 230 in a clockwise or counterclockwise direction according to the operations of the components of the driving part 300. An explanation of such a process will be given later.

Referring back to FIGS. 2 to 3b, the cartridge 200 is detachably attached to the coupling groove 111 of the main body 110, and as the tubes are coupled to the inlet 240 and the outlet 250 of the cartridge 200, respectively, the main body 110 has at least one or more guide members 113 adapted to fit the tubes thereto to prevent the tubes from moving in the process where the chemical liquid or blood flows along the tubes.

Further, a membrane filter 800 is mounted on at least one of the inlet 240 and the outlet 250 of the cartridge 200 to remove air from the chemical liquid.

In a process where the chemical liquid is stored, air may be naturally generated from the chemical liquid, and otherwise, in a process of injecting the chemical liquid, air may be artificially generated. So as to inject the chemical liquid into the patient's body, accordingly, air has to be preremoved. In conventional practices, air is removed from the chemical liquid by a manual operation of a nurse, which increases his or her work load, but according to the present invention, air is automatically removed from the chemical liquid through the membrane filter 800 mounted on at least one of the inlet 240 and the outlet 250 of the cartridge 200, thereby decreasing the nurse's work load.

In specific, the membrane filter 800, which is mounted on at least one of the inlet 240 and the outlet 250 of the cartridge 200, includes a hydrophilic membrane filter for passing the chemical liquid therethrough, not passing air therethrough, and a hydrophobic membrane filter for emitting the air not passing through the hydrophilic membrane filter to the outside.

If the membrane filter 800 is mounted on the inlet 240, it removes air from the chemical liquid introduced into the cartridge 200.

Contrarily, if the membrane filter 800 is mounted on the outlet 250, air, which is pushed by the pressure generated when the tube is pressurized, is removed through the hydrophobic membrane filter. A portion of the tube may be pressurized by means of a bubble detection sensor 115 as will be discussed later for sensing whether air bubbles exist or not, and accordingly, the membrane filter 800, which is mounted on the outlet 250, easily removes the air pushed by the pressure generated from the pressurized tube through the hydrophobic membrane filter.

Figure 14:
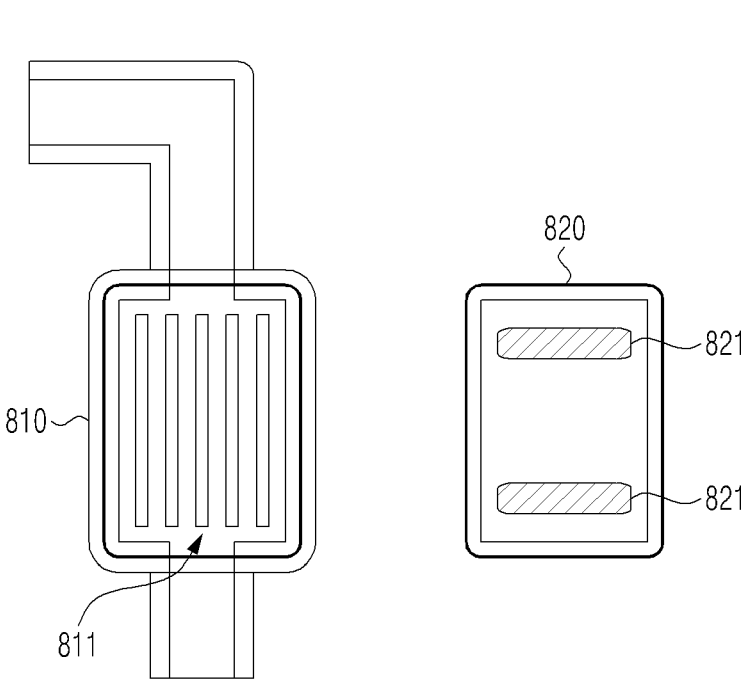
FIG. 14 is a plan view showing a membrane filter of the cylinder pump according to the present invention.

FIG. 14 is a plan view showing the membrane filter of the cylinder pump according to the present invention. Referring to FIG. 14, the membrane filter 800 includes a filter body 810 and a filter cover 820.

The filter body 810 has body slots 811 along which the chemical liquid flows, and the hydrophilic membrane filter is fused onto the middle-end of the filter body 810 to pass only the chemical liquid therethrough.

Further, the filter cover 820 has cover holes 821 onto which the hydrophobic membrane filters are fused. That is, the filter cover 820 emits the air not passing through the hydrophilic membrane filter of the filter body 810 to the outside through the cover holes 821. At least one or more cover holes 821 are formed on the filter cover 820 to gently remove the air from the chemical liquid.

According to the present invention, the membrane filter 800 is configured to couple the filter body 810 and the filter cover 820 to each other so that the air not passing through the hydrophilic membrane filter of the filter body 810 is emitted from the chemical liquid to the outside through the hydrophobic membrane filters on the filter cover 820.

Further, the main body 110 has the bubble detection sensor 115 disposed thereon to detect whether air bubbles are generated in the tube coupled to the outlet 250 of the cartridge 200.

The bubble detection sensor 115 is formed of an ultrasonic or infrared sensor, and when air is generated in the tube, the bubble detection sensor 115 detects changes in the transmittance of ultrasonic waves or infrared rays to sense whether air bubbles are generated in the tube.

Accordingly, the air is primarily removed from the chemical liquid or blood through the membrane filter 800 mounted on the inlet 240 of the cartridge 200, and next, it can be secondarily checked whether the air is completely removed through the bubble detection sensor 115.

Further, the main body 110 includes a blocking detection sensor 114 mounted thereon to detect whether the chemical liquid or blood is blocked in the cartridge 200.

In this case, the blocking detection sensor 114 is a kind of a pressure sensor to sense changes in the internal pressure of the tube coupled to the cartridge 200, and if the internal pressure of the tube is drastically increased, the blocking detection sensor 114 detects that blocking occurs.

Next, the driving part 300 located inside the main body 110 to operate the first piston 260 and the second piston 270 of the cartridge 200 individually will be explained with reference to FIGS. 7 and 8.

Figure 7:
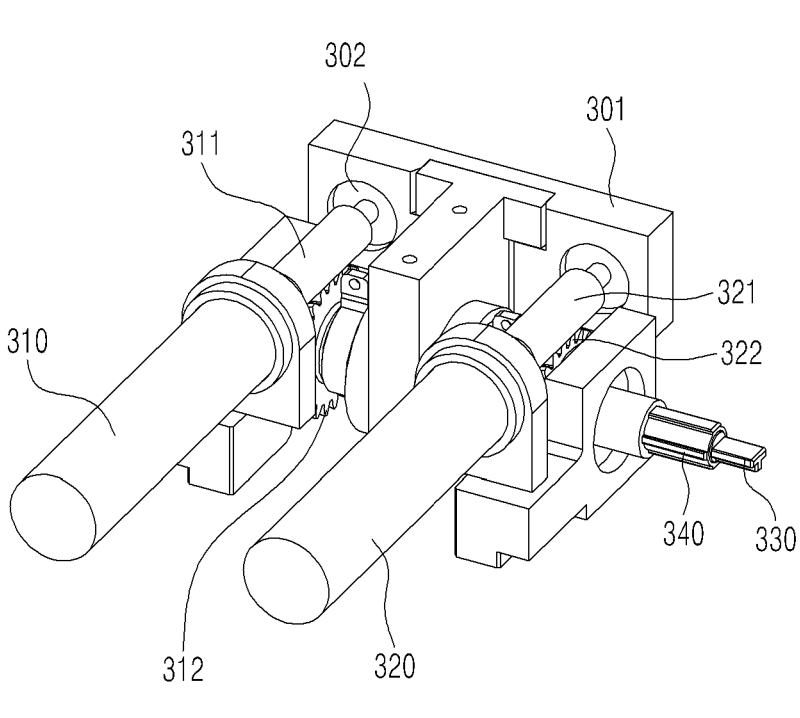
FIG. 7 is a perspective view showing a driving part for operating the cartridge of the cylinder pump according to the present invention.
Figure 8:
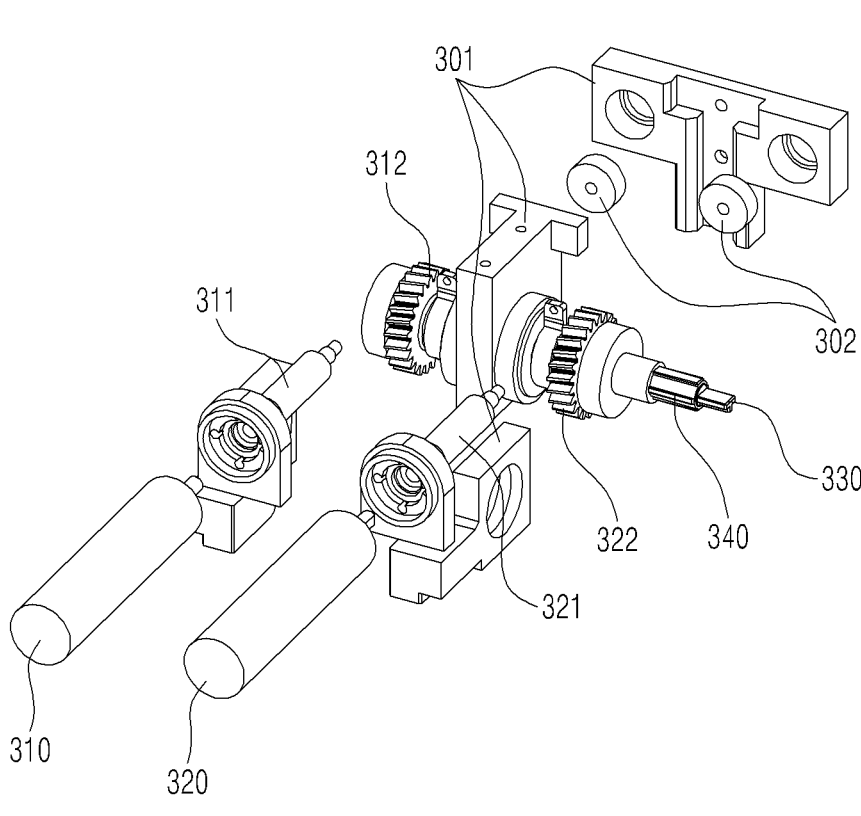
FIG. 8 is an exploded perspective view showing the driving part for operating the cartridge of the cylinder pump according to the present invention.

FIG. 7 is a perspective view showing the driving part for operating the cartridge of the cylinder pump according to the present invention, and FIG. 8 is an exploded perspective view showing the driving part for operating the cartridge of the cylinder pump according to the present invention.

The driving part 300 includes a driving part body 301 and a first driving motor 310 and a second driving motor 320 coupled to the driving part body 301 to generate power therefrom.

Further, the driving part 300 includes a first worm 311, a second worm 321, a first worm gear 312, and a second worm gear 322 that are coupled to the driving part body 301. The first worm 311 is coupled to a rotary shaft of the first driving motor 310 and thus rotates through the rotation of the first driving motor 310, and through the rotation of the first worm 311, the first worm gear 312 engaged with the first worm 311 rotates.

In the same manner as above, the second worm 321 is coupled to a rotary shaft of the second driving motor 320 and thus rotates through the rotation of the second driving motor 320, and through the rotation of the second worm 321, the second worm gear 322 engaged with the second worm 321 rotates. In this case, an inner driving gear 330 is fitted to a rotary shaft to which the first worm gear 312 is coupled, and through the rotation of the first worm gear 312, the inner driving gear 330 rotates. Further, an outer driving gear 340 is fitted to a rotary shaft to which the second worm gear 322 is coupled, and through the rotation of the second worm gear 322, the outer driving gear 340 rotates.

Under the above-mentioned configuration, the driving part 300 is configured to rotate the inner driving gear 330 through the first driving motor 310 and to rotate the outer driving gear 340 through the second driving motor 320. In this case, the outer driving gear 340 is coupled to the upper rotation member 211 through the upper rotation member hole 212 of the cartridge 200, and through the rotation of the first driving motor 310, it rotates the upper rotation member 211. Further, the inner driving gear 330 is coupled to the lower rotation member 221 through the lower rotation member hole 222 of the cartridge 200, and through the rotation of the second driving motor 320, it rotates the lower rotation member 221.

If the upper rotation member 211 rotates, further, the first piston 260 rotates in the clockwise or counterclockwise direction by means of the upper pushing member 213, and if the lower rotation member 221 rotates, the second piston 270 rotates in the clockwise or counterclockwise direction by means of the lower pushing member 223, so that through the rotations of the first driving motor 310 and the second driving motor 320, the first piston 260 and the second piston 270 of the cartridge 200 rotate individually.

In this case, as shown in FIG. 8, the driving part body 301 further includes at least one or more bearings 302 adapted to prevent the first worm 311 and the second worm 321 rotating by means of the first driving motor 310 and the second driving motor 320 from being damaged.

Further, the cartridge 200 is configured to allow the first piston 260 and the second piston 270 to be fixed in position in a production step thereof so as to control an infusion cycle upon an initial operation as will be discussed later. In the conventional practices, however, both of the upper rotation member hole 212 and the lower rotation member hole 222 of the cartridge 200 have the shape of a cross (+), which may cause the cartridge 200 to be erroneously mounted into the coupling groove 111.

If the cartridge 200 is erroneously mounted into the coupling groove 111, the first piston 260 and the second piston 270 are misalignedly located from the positions operating initially by the controller, so that the pistons may collide or be damaged due to the malfunctions of the cylinder pump.

To solve such conventional problems, the cylinder pump according to the present invention is configured to allow the lower rotation member hole 222 to have the shape of T, thereby primarily decreasing the erroneous mounting possibility of the cartridge 200, and further, it is configured to allow the upper rotation member hole 212 to have the shape of a cross having different widths, thereby secondarily decreasing the erroneous mounting possibility of the cartridge 200.

Further, the inner driving gear 330 coupled to the lower rotation member 221 has the shape of T, in the same manner as the lower rotation member hole 222, and the outer driving gear 340 coupled to the upper rotation member 211 has the shape of a cross having different widths, in the same manner as the upper rotation member hole 212.

As the inner driving gear 330 and the outer driving gear 340 of the driving part 300 are coupled to the cartridge 200 (in specific, the lower rotation member 221 and the upper rotation member 211), the entire cartridge 200 including the upper rotation member 211 and the lower rotation member 221 rotates in the clockwise or counterclockwise direction through the rotations of the inner driving gear 330 and the outer driving gear 340. In specific, the cartridge 200 coupled to the coupling groove 111 of the main body 110 rotates in a process of introducing the chemical liquid or blood thereinto or discharging the chemical liquid or blood introduced thereinto to the outside.

While the cartridge 200 is rotating, further, it may escape from the driving part 300 by means of a centrifugal force generated therefrom, but so as to prevent the cartridge 200 from escaping from the driving part 300, the cylinder pump according to the present invention is configured to allow the cartridge 200 to be automatically locked onto the main body 110 when the cartridge 200 is coupled to the coupling groove 111.

Now, an explanation of the locking process of the cartridge 200 will be given in detail with respect to FIGS. 9*a* and 9*b*. First, the outer peripheral surface of the coupling groove 111 is larger than that of the cartridge 200 so that the cartridge 200 is coupled to the coupling groove 111. At the time when the cartridge 200 is initially coupled to the coupling groove 111, as shown in FIG. 9*a*, the cartridge 200 does not come into contact with the inner peripheral wall of the coupling groove 111, and accordingly, the cartridge 200 may be detached from the main body 110 by means of the centrifugal force generated from the rotation thereof.

Figure 9:
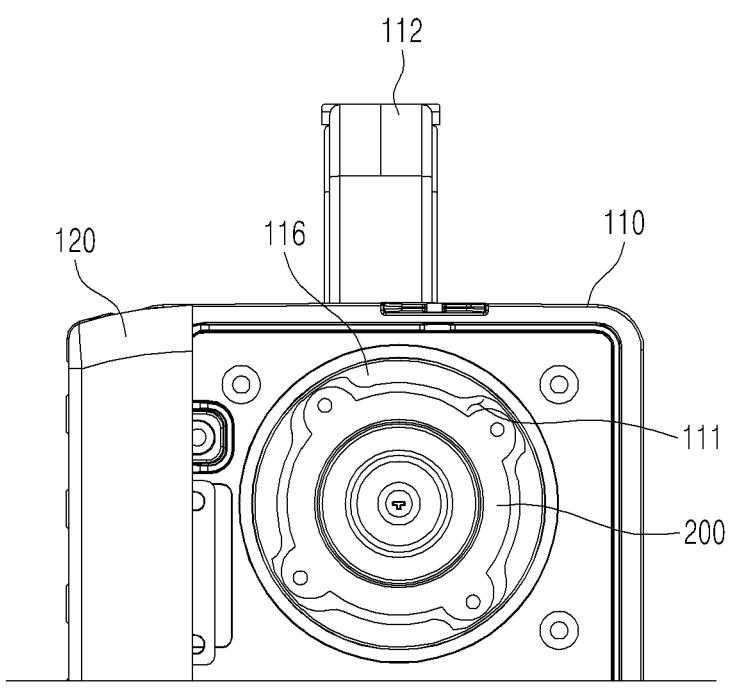
FIGS. 9a and 9b are front views showing a process in which the cartridge is automatically locked onto the cylinder pump according to the present invention when coupled.
Figure 9:
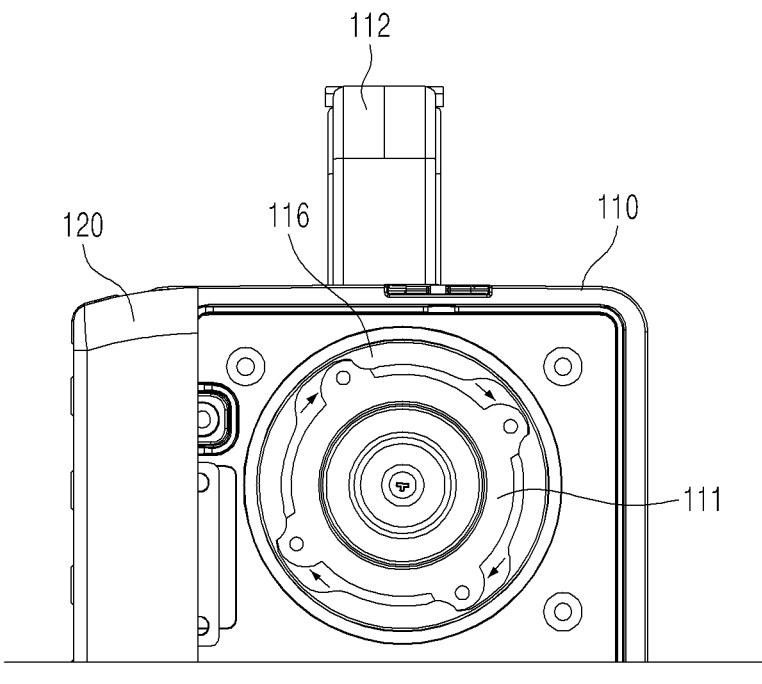
Figure 10:
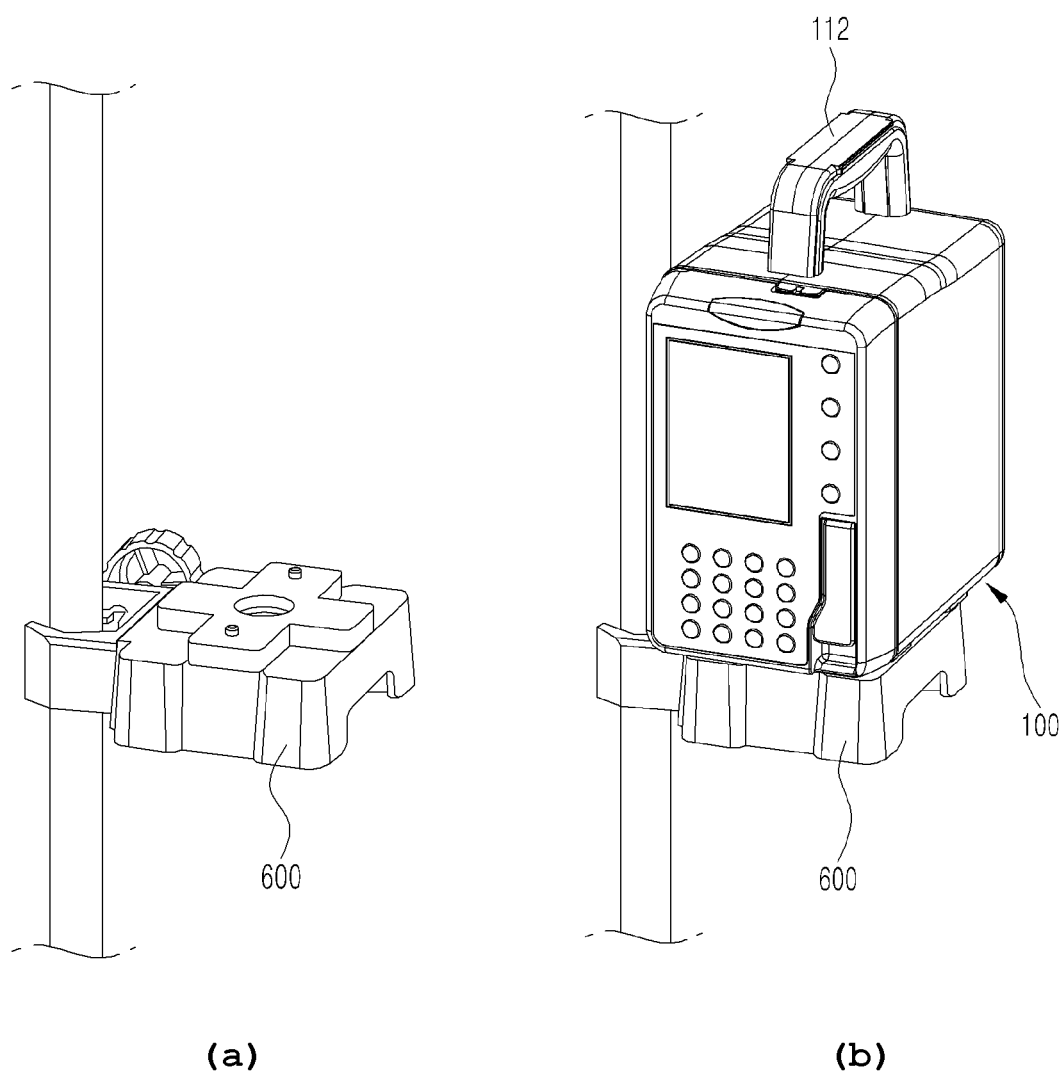
FIGS. 10a and 10b are perspective views showing a state where the cylinder pump according to the present invention is coupled to a clamp.
Figure 11:
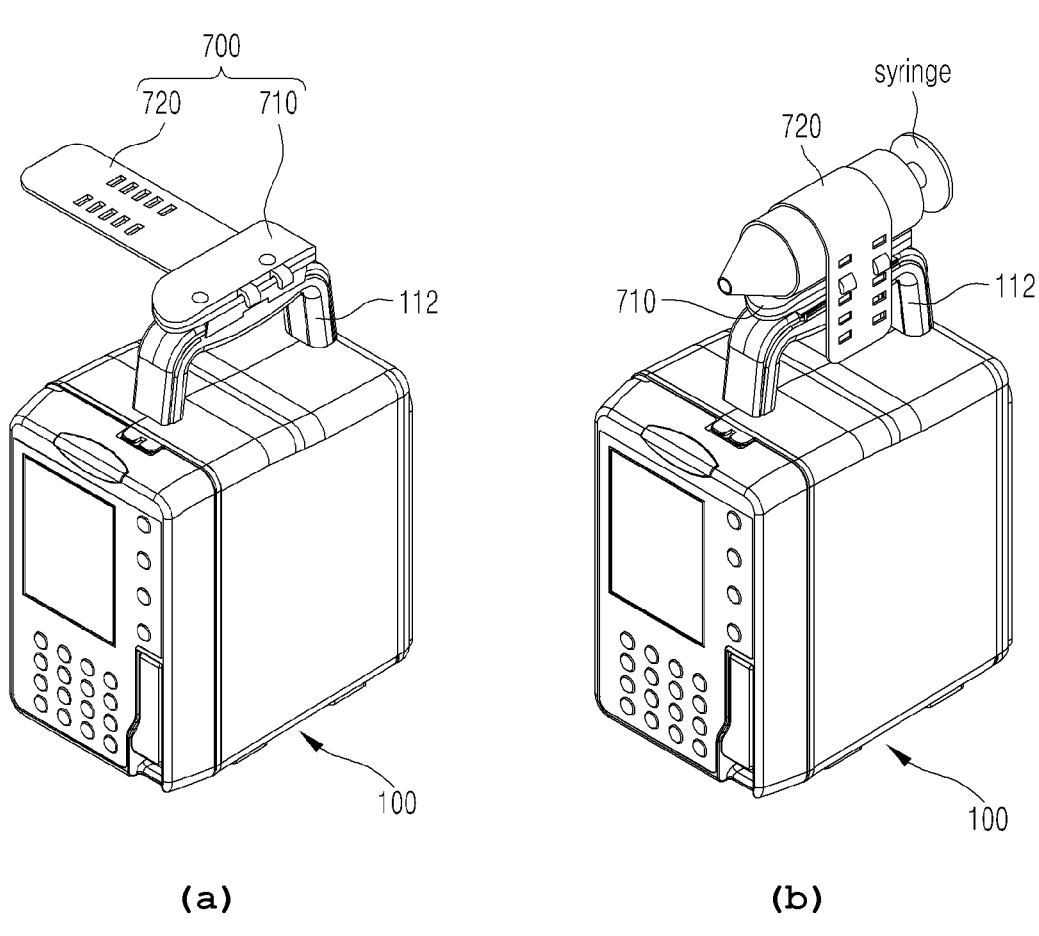
FIGS. 11a and 11b are perspective views showing a state where the cylinder pump according to the present invention is coupled to a syringe holder and a syringe, respectively.
Figure 12:
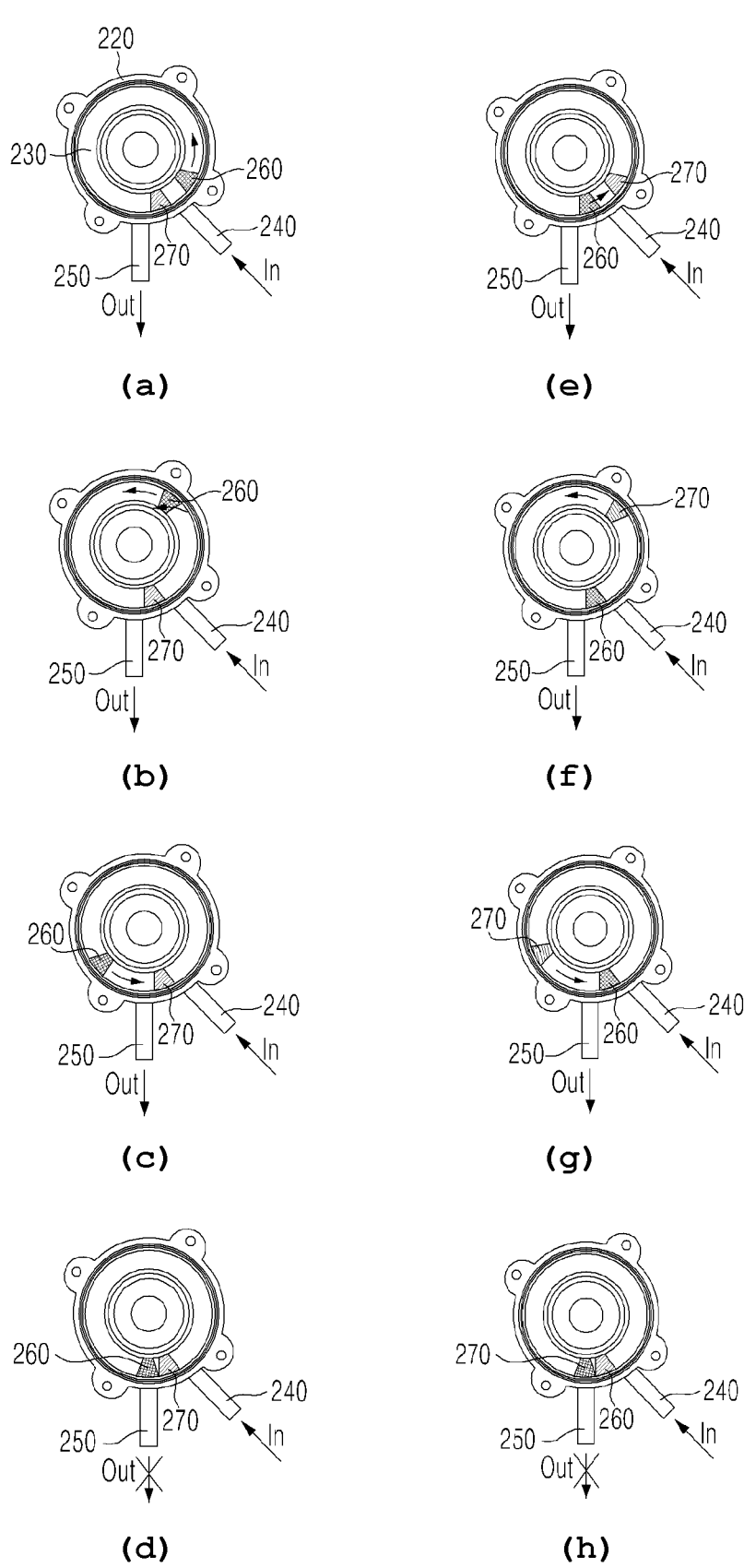
FIGS. 12a to 12h are bottom views showing processes of operating a first piston and a second piston at the inside of the cartridge of the cylinder pump according to the present invention.
Figure 13:
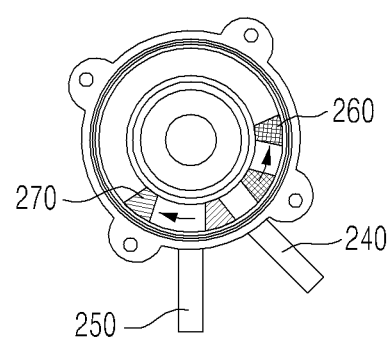
FIGS. 13a to 13c are bottom views showing processes of operating the first piston and the second piston to prime a chemical liquid or blood when the cylinder pump according to the present invention operates in a syringe mode.
Figure 13:
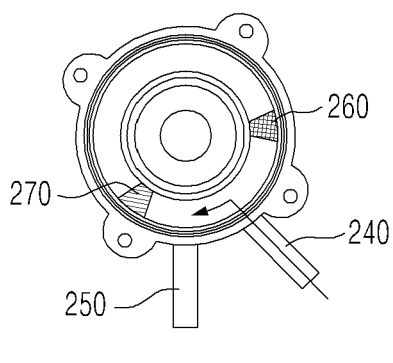
Figure 13:
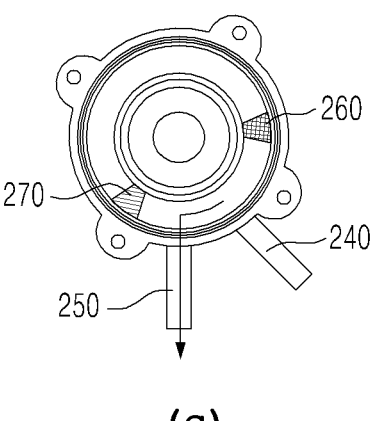

So as to solve such a problem, as shown in FIG. 9*b*, the cartridge 200 rotates in the clockwise or counterclockwise direction through the rotation of the driving part 300 to come into contact with the inner peripheral wall of the coupling groove 111 when it is initially coupled to the coupling groove 111. The process wherein the cartridge 200 comes into contact with the inner peripheral wall of the coupling groove 111 is called "automatic locking" in the present invention.

If the cartridge 200 comes into contact with the inner peripheral wall of the coupling groove 111 through the automatic locking, a blocking force is generated between the inner peripheral wall of the coupling groove 111 and the cartridge 200, thereby preventing the cartridge 200 from being detached from the main body 110 due to the centrifugal force generated from the rotation of the cartridge 20. As a result, the cartridge 200 can be prevented from being damaged due to the detachment from the main body 110.

After the automatic locking of the cartridge 200, of course, the cartridge 200 itself does not rotate, but the upper rotation member 211 and the lower rotation member 221 are kept rotating. An explanation of the process where the chemical liquid or blood is introduced into or discharged from the cartridge 200 through the rotations of the internal components of the cartridge 200 will be given later.

Further, as shown in FIGS. 9*a* and 9*b*, the main body 110 has locking projections 116, and even though the cartridge 200 is coupled to the coupling groove 111 and automatically locked thereonto, it may be detached by the centrifugal force during the rotation thereof through the operation of a motor or arbitrarily detached by the user. However, as shown in FIG. 9b, the locking projections 116 serve to hide given portions of the cartridge 200 to perfectly prevent the cartridge 200 from being detached from the coupling groove 111.

Next, an explanation of exemplary embodiments wherein the chemical liquid or blood is injected through the cylinder pump according to the present invention will be given in detail with respect to FIGS. 10a to 11b.

FIGS. 10a and 10b are perspective views showing a state where the cylinder pump according to the present invention is coupled to a clamp, and FIGS. 11a and 11b are perspective views showing a state where the cylinder pump according to the present invention is coupled to a syringe holder and a syringe, respectively.

The cylinder pump according to the present invention operates in an infusion mode and a syringe mode according to types of containers in which the chemical liquid or blood is stored. In specific, if the chemical liquid or blood is stored in a chemical liquid container or blood pack, the cylinder pump according to the present invention operates in the infusion mode, and contrarily, if the chemical liquid or blood is stored in a syringe, the cylinder pump according to the present invention operates in the syringe mode.

As mentioned above, in the conventional practices, so as to inject the chemical liquid or blood stored in the chemical liquid container or blood pack into the patient's body, the infusion pump has to be used, and so as to inject the chemical liquid or blood stored in the syringe into the patient's body, the syringe pump has to be used. Accordingly, such different devices have to be prepared selectively according to the types of containers in which the chemical liquid or blood is stored.

According to the present invention, however, the chemical liquid or blood is injected into the patient's body with a high degree of precision through only one cylinder pump, while not divided into that stored in the chemical liquid container or blood pack and that stored in the syringe, which makes the cylinder pump according to the present invention differentiated from the conventional chemical liquid injection devices.

In specific, as shown in FIG. 10a, the cylinder pump according to the present invention further includes a clamp 600 coupled to the underside of the body part 100 so that the cylinder pump can be fixed to a stand, and as shown in FIG. 10b, the cylinder pump fixed to the stand through the clamp 600 injects the chemical liquid or blood stored in the chemical liquid container or blood pack attached to the top end of the stand into the patient's body.

Further, as shown in FIG. 11a, the cylinder pump according to the present invention further includes a syringe holder 700 for fixing a syringe to top of the handle 112 of the main body 110 and having a fixing plate 710 and a band 720, and as shown in FIG. 11b, after the syringe is fixed to top of the handle 112 through the band 720, the cylinder pump according to the present invention injects the chemical liquid or blood stored in the syringe into the patient's body.

In this case, the controller collects at least one or more pieces of information of drug information, drug injection speed, drug injection time, drug injection amount, the patient's body weight, and operating mode from the operating part 500 and controls the driving part 300 based on the collected information to thus operate the cartridge 200. In specific, the controller dividedly controls the driving part 300 in the infusion mode and the syringe mode according to the operating mode information transmitted from the operating part 500.

If the cylinder pump is fixed to the stand by means of the clamp 600, the information of the cylinder pump currently operating in the infusion mode through the operating part 500 controlled by the user is inputted to the controller, and accordingly, the controller operates the driving part 300 to the infusion mode, so that the chemical liquid or blood stored in the chemical liquid container or blood pack is introduced into the cartridge 200 or discharged to the outside from the cartridge 200.

If the syringe is fixed to top of the cylinder pump through the syringe holder 700, the information of the cylinder pump currently operating in the syringe mode through the operating part 500 controlled by the user is inputted to the controller, and accordingly, the controller operates the driving part 300 to the syringe mode, so that the chemical liquid or blood stored in the syringe is introduced into the cartridge 200 or discharged to the outside from the cartridge 200.

In this case, an explanation of the process in which the chemical liquid or blood is introduced into the cartridge 200 or discharged to the outside from the cartridge 200 under the control of the driving part 300 through the controller will be given in detail with reference to FIGS. 12a to 13c.

FIGS. 12a to 12h are bottom views showing processes of operating the first piston and the second piston at the inside of the cartridge of the cylinder pump according to the present invention, and FIGS. 13a to 13c are bottom views showing processes of operating the first piston and the second piston to prime the chemical liquid or blood when the cylinder pump according to the present invention operates in the syringe mode.

Though FIGS. 12a to 13c just show the first piston 260 and the second piston 270 operating with respect to the lower housing 220 for the conveniences of the description, but of course, the lower housing 220 is coupled to the upper housing 210 to constitute the cartridge 200.

The cylinder pump according to the present invention is configured to allow the first piston 260 and the second piston 270 to rotate through the driving part 300 so that the chemical liquid or blood is introduced into the cartridge 200 or discharged to the outside from the cartridge 200. The process includes an infusion cycle and an alternation cycle.

For example, when the cylinder pump according to the present invention initially operates, as shown in FIG. 12a, so as to perform the infusion cycle the controller fixes the second piston 270 between the inlet 240 and the outlet 250 in a state of being stopped and rotates the first piston 260 located close to the inlet 240 in the counterclockwise direction, so that a negative pressure is formed in the space of the cylinder 230 between the first piston 260 and the second piston 270 to thus allow the chemical liquid or blood to be introduced into the cartridge 200 through the inlet 240.

Further, as shown in FIGS. 12b and 12c, as the first piston 260 is kept rotating in the counterclockwise direction, the chemical liquid or blood is introduced into the cartridge 200 through the inlet 240, and the chemical liquid or blood in the cylinder 230 is discharged to the outside of the cartridge 200 through the outlet 250. As a result, the chemical liquid or blood moves (that is, is introduced and discharged).

In this case, as shown in FIG. 12d, if the first piston 260 rotates and is thus located on the outlet 250, the chemical liquid or blood in the cylinder 230 is not discharged to the outside of the cartridge 200. In this case, the controller operates the first piston 260 and the second piston 270 at the same time, and as shown in FIG. 12e, the first piston 260 is located between the inlet 240 and the outlet 250, at which the second piston 270 has been located before, and the second piston 270 rotates in the counterclockwise direction, so that the alternation cycle is performed to change the operations of the first piston 260 and the second piston 270 to each other.

After the alternation cycle has been performed, as shown in FIGS. 12f and 12g, the controller performs the injection cycle through which the second piston 270 rotates in the counterclockwise direction in a state where the first piston 260 is fixed, and as the second piston 270 rotates in the counterclockwise direction, the chemical liquid or blood is introduced into the cartridge 200 through the inlet 240, and the chemical liquid or blood in the cylinder 230 is discharged to the outside of the cartridge 200 through the outlet 250.

Further, as shown in FIG. 12h, if the second piston 270 rotates and reaches the outlet 250, the controller performs the alternation cycle again, and accordingly, the controller operates the first piston 260 and the second piston 270 at the same time. As shown in FIG. 12a, the first piston 260 rotates in the counterclockwise direction, and the second piston 270 is located between the inlet 240 and the outlet 250, at which the first piston 260 has been located before, so that the chemical liquid or blood moves repeatedly.

In specific, the controller performs the injection cycle and the alternation cycle based on the information of the drug information, drug injection speed, drug injection time, and drug injection amount. Upon the injection cycle, the controller controls the rotation speeds of the first driving motor 310 and the second driving motor 320 to satisfy the user's desired chemical liquid or blood injection amount and speed, and if the drug injection amount reaches a target chemical liquid or blood injection amount even in a state where the injection cycle is not completely finished, the controller stops driving the first driving motor 310 and the second driving motor 320, thereby finishing the injection cycle.

Upon the alternation cycle, the controller rotates the first driving motor 310 and the second driving motor 320 at the same time to allow them to be located at their target position.

According to the present invention, in this case, the positions of the first piston 260, the second piston 270, the inlet 240, and the outlet 250, as shown in FIGS. 12a to 12h, are just exemplary. Accordingly, the positions of the first piston 260 and the second piston 270 may be changed to each other, the positions of the inlet 240 and the outlet 250 may be changed to each other, and the first piston 260 or the second piston 270 may rotate in the clockwise direction, not in the counterclockwise direction.

If the cylinder pump according to the present invention operates in the syringe mode, the negative pressure is generated in the cylinder 230 of the cartridge 200 by means of the operations of the first piston 260 and the second piston 270, and through the generation of the negative pressure, the chemical liquid or blood stored in the syringe is injected into the cartridge 200, without having any horizontal movement of the syringe's plunger.

However, if the cylinder pump according to the present invention operates in the infusion mode, a priming process of pre-filling the chemical liquid or blood before the injection cycle and the alternation cycle has to be performed to inject the chemical liquid or blood into the patient's body, irrespective of the position of the chemical liquid container or blood pack.

The priming process is the process in which the tubes connected to the inlet 240 and the outlet 250 are pre-filled with the chemical liquid or blood, and so as to allow the tubes to be pre-filled with the chemical liquid or blood, the controller operates the first driving motor 310 and the second driving motor 320, respectively. Accordingly, as shown in FIG. 13a, the first piston 260 of the cartridge 200 is located outside the inlet 240, and the second piston 270 outside the outlet 250, so that there are no pistons between the inlet 240 and the outlet 250.

If the first piston 260 and the second piston 270 are located outside the inlet 240 and the outlet 250, respectively, a negative pressure in the cylinder 230 is generated, and as shown in FIG. 13b, the chemical liquid or blood is introduced into the cylinder 230 through the inlet 240. Unlike when the alternation cycle is performed, when the priming process is performed no piston is fixed to the space between the inlet 240 and the outlet 250, so that as shown in FIG. 13c, the chemical liquid or blood introduced through the inlet 240 is directly discharged to the outside of the cartridge 200 through the outlet 250, thereby removing air from the tube connected to the outlet 250 and filling the tube with the chemical liquid or blood.

If the tube is filled with the chemical liquid or blood through the priming process, further, the first driving motor 310 operates until the first piston 260 is located between the inlet 240 and the outlet 250 and then stops, thereby preventing medical accidents from occurring due to the carelessness of the use of the conventional infusion or syringe pump.

In the state where the tubes connected to the inlet 240 and the outlet 250 are pre-filled with the chemical liquid or blood, as mentioned above, even though the installation position of the chemical liquid container or blood pack is changed, while the cylinder pump according to the present invention is operating in the infusion mode, the chemical liquid or blood filled in the tubes is injected into the patient's body.

In the priming process as mentioned above, the process in which the controller allows the first piston 260 of the cartridge 200 to be located outside the inlet 240 and allows the second piston 270 to be located outside the outlet 250 so that there are no pistons between the inlet 240 and the outlet 250 is a process in which the controller allows the chemical liquid or blood to freely flow in the cartridge 200.

The free flow of the chemical liquid or blood in the cartridge 200 through the control of the controller is used in other processes of the cartridge 200 as well as the priming process.

Through the free flow, first, the compatibility of the cartridge 200 of the cylinder pump according to the present invention with other types of infusion pumps can be ensured. In the case of the infusion pump, that is, the tube is pressurized to inject the chemical liquid or blood, and if the cartridge 200 connected to the tube is in a free flow state, accordingly, it may be compatible with other types of infusion pumps.

Further, in the case where the patient who receives the chemical liquid or blood from the cylinder pump according to the present invention has a magnetic resonance imaging (MRI) or computed tomography (CT) test during which all types of electronic devices as well as the cylinder pump according to the present invention are not carried with him or her, the cylinder pump according to the present invention locates the pistons appropriately to allow the chemical liquid or blood to freely flow in the cartridge 200. The cartridge 200 operating in the free flow state is detached from the cylinder pump by the patient, and a regulator is mounted on the tube, so that even in the case of the MRI or CT test, the injection of the chemical liquid or blood can be consistently maintained.

Further, the operating part 500 is controlled by the user, and accordingly, the controller operates the first driving motor 310 to allow the first piston 260 to be located between the inlet 240 and the outlet 250, so that the chemical liquid or blood does not flow freely. In specific, the cylinder pump according to the present invention prevents the occurrence of the incidental injection of the chemical liquid or blood into the patient's body if the coupling between the main body 110 and the front body 120 is released (that is, if the front body 120 is open), thereby ensuring the safety of the patient.

The free flow of the chemical liquid or blood in the cartridge 200 may cause the chemical liquid or blood to be incidentally injected into the patient's body, which makes the patient not safe. Accordingly, it should be understood that the free flow of the chemical liquid or blood in the cartridge 200 is selectively performed through the control of the operating part 500 by the user.

As mentioned above, the cylinder pump according to the present invention can ensure the compatibility of the cartridge 200 with other types of infusion pumps through the free flow of the chemical liquid or blood, and in addition thereto, the cylinder pump according to the present invention can ensure the compatibility of the cartridge 200 with the same types of cylinder pumps through the coordinates of the pistons.

In specific, the patient who receives the chemical liquid or blood from the cylinder pump according to the present invention may receive the chemical liquid or blood from the same type of other cylinder pump.

For example, in the case of a large hospital, medical devices are disposed and managed every ward, and the patient who moves to another ward from his or her ward has to use another cylinder pump of the same type as used before, which belongs to the new ward.

In this case, the patient's cartridge 200 is still used in another cylinder pump of the same type, without any exchange with a new cartridge 200.

The compatibility of the cartridge 200 with another cylinder pump of the same type is acquired by sharing the coordinates of the pistons between the cylinder pumps.

A process of sharing the coordinates of the pistons between the cylinder pumps is as follows. First, the controller of the cylinder pump receives the coordinates of the first piston and the second piston of the cartridge 200 during the injection cycle or the alternation cycle for the injection of the chemical liquid or blood from the operating part and then displays the received coordinates on the display part 400. Next, after the coordinates of the pistons displayed on the display part 400 are checked, the cartridge 200 is detached from the cylinder pump by the user, and the coordinates are inputted to another cylinder pump onto which the cartridge 200 is going to be mounted. The controller of the cylinder pump onto which the cartridge 200 is going to be mounted allows the position of the coupling groove 111 to be aligned with the positions of the upper rotation member hole 212 and the lower rotation member hole 212 of the detached cartridge 200 in accordance with the coordinates of the pistons received from the user.

Next, the cartridge 200 is mounted into the coupling groove 111 of the new cylinder pump which is aligned with the upper rotation member hole 212 and the lower rotation member hole 212 thereof, and accordingly, the injection of the chemical liquid or blood, which is stopped in the cylinder pump before, can be performed again.

While the foregoing examples are illustrative of the principles according to the present invention in one or more particular applications, it will be apparent to those of ordinary skill in the art that numerous modifications in form, usage and details of implementation can be made without the exercise of inventive faculty, and without departing from the principles and concepts of the invention.

Terms used in this application are used to only describe specific exemplary embodiments and are not intended to restrict the present invention. An expression referencing a singular value additionally refers to a corresponding expression of the plural number, unless explicitly limited otherwise by the context.

It is therefore intended that the scope of the invention be limited not by this detailed description, but rather by the claims appended hereto.

| [Explanations of Reference Numerals in the Drawings] | |
| --- | --- |
| 100: Body part | 110: Main body |
| 111: Coupling groove | 112: Handle |
| 113: Guide member sensor | 114: Blocking detection sensor |
| 115: Bubble detection | 116: Locking projection |
| 120: Front body | |
| 200: Cartridge | 209: Upper housing hole |
| 210: Upper housing | 211: Upper rotation member |
| 212: Upper rotation member hole | 213: Upper pushing member |
| 220: Lower housing | 221: Lower rotation member |
| 222: Lower rotation member hole | 223: Lower pushing member |
| 230: Cylinder | 240: Inlet |
| 250: Outlet | 260: First piston |
| 270: Second piston | 300: Driving part |
| 301: Driving part body | 302: Bearing |
| 310: First driving motor | 311: First worm |
| 312: First worm gear | 320: Second driving motor |
| 321: Second worm | 322: Second worm gear |
| 330: Inner driving gear | 340: Outer driving gear |
| 400: Display part | 500: Operating part |
| 600: Clamp | 700: Syringe holder |
| 710: Fixing plate | 720: Band |
| 800: Membrane filter | 810: Filter body |
| 820: Filter cover | 811: Body slot |
| 821: Cover hole | |

The invention claimed is:

1. A cylinder pump comprising:

a body part having a main body with a coupling groove formed thereon and a front body coupled to the main body by means of hinges;

a cartridge detachably attached to the coupling groove of the body part;

a driving part located inside the main body to operate the cartridge and comprising at least one driving motor and a gear mechanism configured to transmit rotational power to rotation members of the cartridge;

a display part located on the front body and configured to visually output operation information for operating the cylinder pump;

a controller comprising a processor and configured to control the operation of the driving part; and an operating part comprising at least one user input key and configured to transmit a user's operating signal or input information to the controller, wherein the cartridge comprises:

an upper housing into which an upper rotation member is inserted; and a lower housing coupled to the upper housing and into which a lower rotation member is inserted, wherein the upper rotation member has an upper rotation member hole formed thereon, the lower rotation member has a lower rotation member hole formed thereon, and a donut-shaped cylinder is formed by inner peripheral surfaces of the upper and lower housings and outer peripheral surfaces of the upper and lower rotation members, the donut-shaped cylinder having an inlet connected thereto to introduce a chemical liquid or blood thereinto, an outlet connected thereto to discharge the chemical liquid or blood therefrom to the outside, and a first piston and a second piston rotating therein.

2. The cylinder pump according to claim 1, wherein the driving part comprises:

a driving part body;

a first driving motor and a second driving motor coupled to the driving part body;

a first worm and a second worm operating by means of the first driving motor and the second driving motor, respectively;

a first worm gear and a second worm gear operating engagedly with the first worm and the second worm, respectively;

an inner driving gear rotating by means of the first worm gear; and an outer driving gear rotating by means of the second worm gear.

3. The cylinder pump according to claim 2, wherein the upper rotation member hole has the shape of a cross having different widths and the lower rotation member hole is in the shape of a T.

4. The cylinder pump according to claim 3, wherein the outer driving gear has the shape of a cross having different widths and is coupled to the upper rotation member, and the inner driving gear is in the shape of a T and is coupled to the lower rotation member.

5. The cylinder pump according to claim 1, wherein the controller acquires coordinates of the first piston and the second piston located inside the cartridge to display the acquired coordinates on the display part.

6. The cylinder pump according to claim 1, wherein the controller controls the driving part to allow the first piston and the second piston of the cartridge to be located at the outsides of the inlet and the outlet so that the chemical liquid or blood freely flows from the cartridge.

7. The cylinder pump according to claim 1, wherein the controller controls the driving part to allow the first piston of the cartridge to be located between the inlet and the outlet so that no chemical liquid or blood freely flows from the cartridge.

8. The cylinder pump according to claim 1, wherein at least one of the inlet and the outlet has a membrane filter mounted thereon to remove air from the chemical liquid.

9. The cylinder pump according to claim 8, wherein the membrane filter comprises a hydrophilic membrane filter for passing the chemical liquid therethrough, not passing air therethrough, and a hydrophobic membrane filter for emitting the air not passing through the hydrophilic membrane filter to the outside.

*    *    *    *    *